United States Patent [19]

Young et al.

[11] 4,345,099

[45] Aug. 17, 1982

[54] METHOD OF SELECTIVELY REMOVING BIURET FROM UREA AND COMPOSITIONS FOR USE THEREIN

[75] Inventors: Donald C. Young, Fullerton; James A. Green, II, Chino, both of Calif.

[73] Assignee: Union Oil Company of California, Los Angeles, Calif.

[21] Appl. No.: 291,428

[22] Filed: Aug. 10, 1981

[51] Int. Cl.³ .................. C07C 127/01; C07C 126/08
[52] U.S. Cl. .......................................... 564/63; 71/28; 71/119; 564/73
[58] Field of Search ..................................... 564/73, 63

[56] References Cited

U.S. PATENT DOCUMENTS

| | | | |
|---|---|---|---|
| 1,951,518 | 3/1934 | Meiser et al. | 564/73 X |
| 2,854,482 | 9/1958 | Guyer | 564/73 |
| 3,185,731 | 5/1965 | Kaasenbrood | 260/555 |
| 3,211,788 | 10/1965 | Cook | 564/73 |
| 3,232,984 | 2/1966 | Finneran | 564/73 X |
| 3,251,879 | 5/1966 | Rosenbloom | 260/555 |
| 3,255,246 | 6/1966 | Singer | 564/73 X |
| 3,287,407 | 11/1966 | Zardi | 564/73 |
| 3,318,951 | 5/1967 | Kaasenbrood | 564/73 |
| 3,903,158 | 9/1975 | Fuentes | 260/555 B |
| 4,231,960 | 11/1980 | Schmidt | 564/73 |

FOREIGN PATENT DOCUMENTS

| | | | |
|---|---|---|---|
| 1468229 | 12/1968 | Fed. Rep. of Germany | 564/73 |
| 1156099 | 6/1969 | United Kingdom | 564/73 |
| 1404098 | 8/1975 | United Kingdom | 564/73 |

OTHER PUBLICATIONS

Chao, "Urea, Its Properties and Manufacture," Chao's Institute, West Covina, Calif. published Taipei, Taiwan.

*Primary Examiner*—John Doll
*Attorney, Agent, or Firm*—Michael H. Laird; Dean Sandford

[57] ABSTRACT

Biuret is selectively removed from urea by treating the urea in an aqueous solution at a pH above about 12.5 and a temperature between about 0° C. and 100° C. for a period of time sufficient to decompose at least a portion of the biuret. Solid urea compositions containing biuret and a strong base capable of selectively decomposing at least a portion of the biuret when the mixture is dissolved in water are also disclosed.

18 Claims, 1 Drawing Figure

METHOD OF SELECTIVELY REMOVING BIURET FROM UREA AND COMPOSITIONS FOR USE THEREIN

BACKGROUND OF THE INVENTION

1. Field of the Invention

This invention relates to methods of reducing the biuret content of urea by reacting an aqueous solution of biuret-containing urea with a strong base to selectively hydrolyze biuret relative to urea, and to urea solutions and solid urea formulations useful in such methods.

Urea is a widely used fertilizer and chemical precursor. Most often it contains some biuret that forms during the manufacturing process or otherwise when urea is heated to 130° C. or above. Biuret can interfere with chemical processing and is toxic to many plants. Biuret phytotoxicity is widely recognized and is regulated or monitored by government agencies and industry. The Indian government prohibits the import of urea containing more than 2 weight percent biuret. The United States agricultural industry generally observes an upper limit of 0.25 weight percent biuret for urea fertilizers classified as "low biuret." This criterion is generally recognized by the citrus and other industries that use urea for foliar fertilization.

Detectable biuret toxicity symptoms have been noted in field tests on lemon and grapefruit in Southern California at biuret levels as low as 0.1 weight percent. Biuret toxicity has also been observed with topically applied urea prills and solutions. Germination inhibition and damage to seedlings has been observed in wheat, barley and similar grain crops at levels of 2 weight percent biuret. These studies, and a comprehensive review of literature available on this subject, are presented by Mithyantha, Kulkarni, Tripathi and Agnihothrudu, Fertilizer News, 1977, pp. 13–18.

Damage to corn has been observed at foliar biuret dosages of 0.2 to 0.5 kilogram per hectare. Thirty percent yield loss was noted in one study at 1.7 kilograms biuret per hectare banded near seeds. Wheat damage has been observed at 0.2 to 0.5 kilogram per hectare foliarly applied with severe toxicity observed at 6.0 kilograms per hectare biuret banded in the soil. Fifteen to twenty ppm soil biuret level has been shown to inhibit barley seed germination while substantial crop damage from foliar application occurs at 0.4 to 0.6 kilogram biuret per hectare.

Similar effects have been observed in rice, citrus, cotton, avocado, beans, soybeans and potatoes, several of which are particularly sensitive to biuret in foliar fertilizers. In citrus, as little as 0.2 kilogram foliarly applied biuret per hectare causes detectable damage. Avocados are damaged by as little as 50 ppm biuret in foliar sprays. As little as 3 kilograms per hectare biuret banded in the soil inhibits potato germination and causes citrus damage in light soils.

In view of these results, it is not surprising that the industry has devoted substantial effort to methods of preventing biuret formation in the first instance, and to methods of reducing its concentration once it is formed. Most present commercial urea plants are capable of producing solid and solution urea containing much less biuret than was previously the case. However, commercial ureas still contain at least 0.5 weight percent biuret almost without exception, and most contain from 1 to 2 weight percent. Biuret content can rise considerably higher if production is not adequately controlled.

2. Description of the Prior Art

One process for removing biuret from urea solutions is described by Fuentes in U.S. Pat. No. 3,903,158, issued Sept. 2, 1975. Fuentes describes a procedure in which a urea solution containing biuret is passed over an ion exchange resin which, according to Fuentes, selectively retains biuret while allowing urea to pass through the exchange column. Although the ion exchange process may be suitable in some applications, it requires specialized apparatus, controls and procedures not readily available or practical in every case. It also converts biuret nitrogen to non-nutrient forms which are lost in the process.

It is, therefore, an object of this invention to provide an improved process for the selective removal of biuret from urea.

It is another object to remove biuret from urea solutions and minimize urea and reactant consumption.

Another object is the production of low biuret urea solutions containing less than 0.25 weight percent biuret based on urea.

Another object is the production of urea solutions containing less than 0.05 weight percent biuret based on urea.

Yet another object is the provision of a method for selectively converting biuret to non-toxic nutrient forms in aqueous urea solutions by base hydrolysis.

Another object is the provision of solid and aqueous compositions for the use in such methods.

Yet another object of this invention is to provide improved urea solutions for agricultural and/or chemical use.

Another object is the provision of solid mixtures of urea and one or more strong bases which, when added to water, will react to selectively eliminate biuret, if present.

Other objects, aspects and advantages of this invention will be apparent to one skilled in the art in view of the following disclosure, the drawing and the appended claims.

SUMMARY OF THE INVENTION

In accordance with one embodiment of the invention, biuret contained in aqueous urea solutions is selectively decomposed, relative to urea, by reaction, at a temperature of 0° C. to about 100° C., with at least one strong base capable of producing a pH of at least 12.5 in said solution for a reaction time sufficient to hydrolyze at least a portion of the biuret. Sufficient base concentration should be maintained to maintain a pH of at least 12.5 for the duration of the reaction.

In accordance with another embodiment, this invention provides aqueous urea solutions containing minor amounts of biuret relative to urea, and at least a 0.1 N concentration of a strong organic or inorganic base capable of producing a pH of at least about 13. The base concentration and pH are sufficient to hydrolyze biuret to products comprising urea, ammonia, or ammonium hydroxide, and carbon dioxide when the solutions are maintained at temperatures between about 0° C. and 100° C.

In accordance with another embodiment, this invention provides improved solid urea compositions suitable for producing the aqueous urea solutions referred to above. The solid compositions can comprise urea in any physical form such as particles, powders, etc., containing biuret and a strong base or base precursor, capable of producing a pH of at least about 13 in an aqueous urea solution.

BRIEF DESCRIPTION OF THE DRAWING

The invention will be more readily understood by reference to the drawing which is a schematic illustration of one process scheme suitable for practicing the methods of this invention.

DETAILED DESCRIPTION OF THE INVENTION

Figure 1:
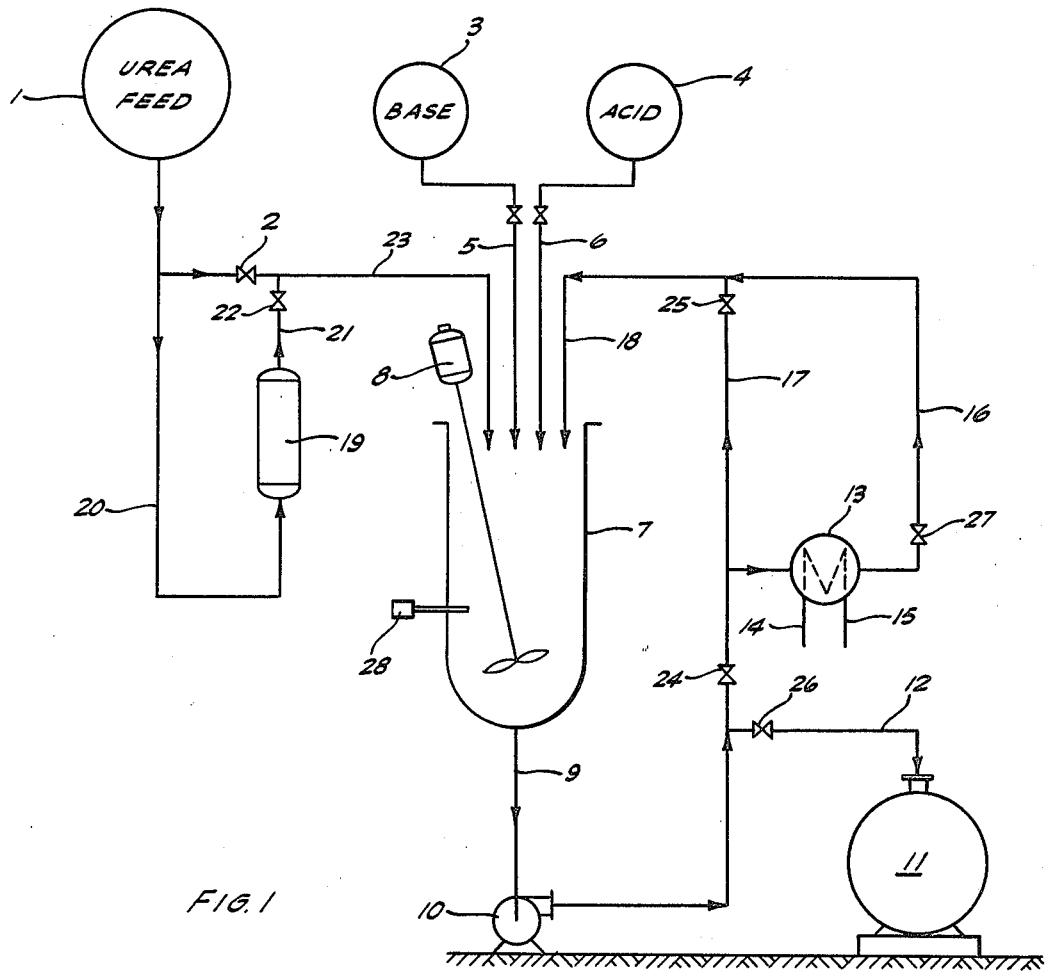

The mineral bases and base precursors are preferred and are preferably selected from the alkali metals or alkali metal compounds, i.e., lithium, sodium, potassium, cerium and rubidium metals or compounds or any combination of these. The solutions and solid compositions may also contain other bases or precursors such as calcium, magnesium, strontium, barium, etc., metals and compounds. Base precursors are compounds of the above listed materials, which, when dissolved in water, produce the corresponding metal base.

Sodium and potassium hydroxides, hydroxide precursors, and their combinations are particularly preferred in both the solid and aqueous compositions and methods. Potassium hydroxide is most preferred when the urea is destined for agronomic application.

The utility of the methods and compositions described herein is actually contraindicated by the studies of previous investigators. At page 122 of his text "Urea, Its Properties and Manufacture," Chao's Institute, West Covina, Calif. published in Taipei, Taiwan, Chao states that biuret is hydrolyzed by hot water, but less rapidly than urea. Accepting that that was the case under the conditions investigated by Chao, it is not the case in the methods described herein. If that condition prevailed in the systems described herein, it would be impossible to selectively remove biuret from urea solutions by hydrolysis. As pointed out above, most commercially available ureas contain from 0.5 to 2 weight percent biuret; some contain substantially higher levels of biuret. If, in the systems herein described, biuret was, as stated by Chao, hydrolyzed less rapidly than urea, the hydrolysis route would cause considerable urea hydrolysis and consumption of added base under the conditions required to reduce the initially low biuret levels to nontoxic proportions.

In further contrast to the teachings of Chao, we have found that biuret is not only selectively eliminated relative to urea, but that it is quantitatively converted to urea. Thus, the conversion of biuret by our process actually contributes to the urea content of the aqueous solution. However, this contribution is usually very minor due to the relatively low biuret concentration of the urea feed.

The solutions of this invention, and those used in these methods, can contain any amount of urea that is soluble at solution temperature; e.g., up to 85 weight percent. Undissolved urea may also be present during treatment. Elevated temperature, e.g., 60° C. or above, are sometimes required to dissolve urea in high concentrations; the solubility limit at reaction temperature is the limiting factor in this respect.

Very low urea concentrations can also be employed. In fact, solutions containing any amount of urea; e.g., 0.5 percent, such as those used in some foliar feeding applications, can also be treated by these methods. However, urea concentrations will generally be between about 1 and about 85 weight percent, preferably at least about 10 weight percent, and usually between about 20 and about 42 weight percent.

The range of 20 to 42 percent includes the urea concentrations most conveniently treated by these methods at the preferred temperature range of 40° C. to 60° C. That concentration range is also suitable for most commercial applications since the upper limit of 42 weight percent corresponds to the urea crystallization point of 0° C.

Furthermore, we have discovered that biuret conversion rate decreases at urea concentrations above 42 weight percent. Thus, higher concentrations are less preferred when high conversion rates are required.

These methods can be employed with solutions containing essentially any amount of biuret. Ordinarily, the reactant solution will contain at least about 0.05, usually at least about 0.1, and most often about 0.5 to about 4 weight percent biuret based on urea. Solid urea, or urea solutions of even higher biuret content, can be treated by these methods. Most commercial ureas generally contain at least 0.5, and often more than about 1 weight percent biuret.

The organic or inorganic bases must be capable of producing a pH of at least about 12.5, preferably at least about 13, and most preferably about 14, in aqueous media. Any other materials, including weaker bases, can also be present. However, sufficient strong base must be present to produce the required pH. The selective biuret removal from aqueous solutions ceases at pH levels below about 12.5.

Although the mineral bases are preferred due to availability, cost, and the fact that some of them are readily convertible to nutrients upon neutralization, organic bases such as tetramethylammonium hydroxide, and others capable of producing the required pH levels, can also be used. The alkali metal hydroxides and their water soluble precursors are preferred, and include lithium, sodium, potassium, cesium, and rubidium hydroxides and hydroxide precursors.

It is essential only that the strong base exist in the solution as such; i.e., in a form capable of producing the high pH required for selective biuret removal. The base can be formed in situ by adding metal compounds such as the oxides or salts that convert to the hydroxide in solution. Preferred compositions include those in which potassium and/or sodium hydroxide constitute at least about 50 weight percent of the total base concentration.

The effective base concentration must be sufficient to obtain the required pH of 12.5. Reaction pH levels of at least 13 are preferred, and pH 14 is most preferred.

An alkali metal base concentration of 0.1 N would produce an initial pH slightly above 12.5. When this minimum concentration is used initially, incremental base addition will probably be required as the reaction proceeds. The need for subsequent base addition can be readily determined by treating a sample of the urea solution with various base compositions at several concentrations, temperatures and reactions times, and determining the extent of biuret reduction in each case by product analysis. Optimum operating conditions for treating the entire feed can then be determined. Also, solution pH and/or biuret content can be periodically or continuously monitored during the process to determine the need for additional base and/or the extent of biuret conversion.

Obviously, the pH and/or temperature can drop below the levels required to obtain significant, or, for that matter, any biuret conversion at one or more times during the process. The addition of strong base and/or elevation of solution temperature to the required levels will reinitiate selective biuret conversion.

Preferred base concentrations, particularly in batch operations, correspond to at least about 0.2, and preferably at least about 0.4 N, added either initially, incrementally or continuously throughout the run. Most presently available commercial ureas can be adequately treated in batch or continuous operations at initial base concentrations of 0.4 to about 1.2 N.

The pH and base normality conditions defined herein also apply to the solid mixtures of urea and base that constitute another embodiment of this invention. In other words, when a preferred minimum base concentration of 0.1 N is referred to, it is also intended to advise the artisan that, when preparing a solid mixture of urea and base, sufficient base should be added so that when the mixture is dissolved in a predetermined amount of water, the resulting base concentration will correspond to at least about 0.1 N.

With respect to the solid mixtures, base concentration can be conveniently expressed in terms of equivalents of strong base per kilogram of urea. For instance, 0.2 equivalents of strong base per kilogram of urea is required to obtain an initial base concentration of about 0.1 N when the urea is dissolved in an equal weight of water to produce a 50 weight percent urea solution. The extrapolation of base equivalents per kilogram of solid urea required to obtain an initial base concentration of 0.1 N at other dilutions is linear. Thus, 0.4 equivalents of strong base per kilogram of urea would be required to obtain a 0.1 N initial base concentration in a solution containing 25 weight percent urea. Similarly, 2 equivalents of strong base per kilogram of urea would be required to obtain a 0.1 N initial base concentration when the solid is dissolved in sufficient water to produce a 5 weight percent urea solution. At least 10 equivalents of base per kilogram of urea should be provided to assure a base concentration of at least about 0.1 N when the mixture is to be dissolved to produce a solution containing 1 weight percent urea.

In short, the solid urea should contain sufficient base to produce an initial pH of at least about 12.5, preferably about 13 to about 14 at the maximum dilution anticipated. As a practical matter the solid urea should contain at least about 0.2, preferably at least about 0.5 and most preferably at least about 1 equivalents of strong base per kilogram of urea. A base concentration of 1 equivalent per kilogram of urea will produce initial base concentrations of 0.1 N and 0.2 N in 10 and 20 weight percent urea solutions, respectively.

The amount of base or base precursor added to solid urea can be calculated to be sufficient to selectively convert a predetermined amount of biuret, or it can be added purely as insurance against undetermined amounts of biuret that may be present. The presence of strong base in the solid urea assures that biuret, if present, will be selectively converted when the urea is mixed with water providing, of course, that the solution is not so dilute that the necessary minimum pH of 12.5 is not achieved in the urea solution.

It is not necessary that the solution be maintained at any particular temperature within the broad range of 0° C. to 100° C., although biuret is more rapidly removed at elevated temperatures, e.g., 45° C. and above, as disclosed elsewhere herein. It will be removed at any temperature and thus, any phytotoxic or otherwise detrimental effects of undetermined amounts of biuret will be mitigated by the use of solid mixtures containing strong base.

For the purpose of this disclosure, effective base concentration connotes the amount of base available to react with biuret, as opposed to the amount, if any, that is required to neutralize other components in the feed. Commercial ureas often contain minor amounts of ammonia or ammonium carbonate which is produced by urea hydrolysis at elevated temperature. Ammonia and ammonium carbonate partially neutralize the base essential to the reaction. Accordingly, sufficient base should be added to neutralize carbonate or other neutralizing agents, if present, and still produce the pH required for reaction.

In the alternative, carbonate anion can be removed from the solution prior to base addition by any one of several procedures which are known for removing or neutralizing carbonates. These procedures include anion exchange, reaction with cations that form insoluble carbonates, and other procedures.

Ion exchange resins suitable for removing carbonate anions include resins marketed by Rohm and Haas Company under the trademarks IRA 400 and IRA 900, and other strongly basic ion exchange resins. Carbonate can be removed by precipitation with a cation that forms insoluble carbonates; e.g., calcium, magnesium, etc. Further examples are given in the solubility tables of chemistry handbooks, such as Lang's Handbook of Chemistry, McGraw-Hill. The precipitating cation can be added in a soluble form such as the base or soluble salt.

Operating temperatures can range from about 0° C. to about 100° C. However, the reaction is very slow at temperatures below 40° C., and urea hydrolysis, which becomes detectable at temperatures above about 60° C., becomes substantial at 70° C. and above. Nevertheless, the desired conversions can be achieved at the lower temperatures within the broad range given sufficient time, and, in many instances, the relatively minor urea losses incurred at the higher temperatures may be tolerable when shorter reaction times, e.g., four hours or less, are desired.

A particularly desirable and unique relationship between the respective biuret and urea hydrolysis rates exists at temperatures of about 60° C. and less. At temperatures below 60° C. urea hydrolysis essentially ceases. Biuret hydrolysis rate decreases much more gradually as a function of temperature when passing through the 60° C. threshold. Thus, base consumption, urea hydrolysis, and product impurity level can be substantially reduced by operating at temperatures at about 60° C. or less. This may be due to an anomalous discontinuity in the urea and biuret reaction rate coefficients at temperatures below 60° C.

Accordingly, the reaction temperature range of about 20° C. to about 80° C. is preferred, 20° C. to about 65° C. is more preferred, and 40° C. to about 60° C. is most preferred. The higher reaction temperatures, e.g., 60° C. and above, require significantly higher hydroxide ion (base) concentrations, particularly in batch operations. For instance, in a batch operation conducted at 60° C., it was necessary to use an initial NaOH concentration of 0.8 N to obtain the degree of biuret conversion achieved at 24° C. with an initial base concentration of only 0.4 N NaOH.

In most cases it is preferable to maintain solution temperature above the urea crystallization point prior to product dilution and cooling. Solution crystallization point should also be kept in mind when determining solution temperature at any stage of the process. Most often it is desirable to prevent crystallization of a solid urea phase during any stage of reaction or cooling unless the operator wishes to recover part of the purified urea in the solid form. It is generally preferable, however, to dilute the solution prior to or during the cooling step to prevent urea precipitation when the urea concentration is so high that the solution has a crystallization point above the anticipated system temperature.

The reaction time required to obtain a given biuret level depends on initial biuret concentration, total urea concentration, reaction temperature, and base composition and concentration. Biuret conversion rate decreases at higher urea concentrations; e.g., above 570 grams per liter (about 50 weight percent) at all temperatures investigated. Also, conversion rate roughly doubles with every 10 degrees centigrade increase in temperature. Thus, the reaction time required to achieve the desired biuret level can be significantly reduced by increasing reaction temperature. However, as discussed above, higher reaction temperatures, e.g., above 60° C. require higher base concentrations and cause some urea loss, particularly when longer reaction times are used to obtain very low biuret levels.

In some instances the operator may prefer to reduce the amount of the base required to achieve target biuret levels at the expense of the longer run time required for lower temperature operation. However, longer reaction times increase capital investment and operating expense; e.g., heat load, etc., for any given production rate. Thus, higher reaction temperatures and/or concentrations may be preferred in other cases. The most desirable set of operating conditions—temperature, base concentration, base composition, and reaction time—can be readily determined by the sample test referred to above.

The optimum reaction time can change substantially due to the factors discussed and the variations in feed biuret levels and product specifications. Most often, however, significant biuret reduction requires reaction times of at least about one hour at the higher base concentrations, pH levels and temperatures.

Ordinarily, reaction times will be at least about 10 hours and are preferably at least about 20 hours. The longer reaction times allow the use of temperatures, pH levels, and base concentrations sufficient to achieve acceptable biuret levels; e.g., 0.1 weight percent biuret based on urea and lower, without excessive heat load, base requirement, or urea loss. If sufficient treating capacity is available, base and urea consumption, and heat load requirements can be reduced by extending reaction time to 40 hours or more. The biuret content of most commercial ureas can be reduced to less than 0.05 weight percent at temperatures of 55° C. to 60° C. with 0.8 to about 1.2 normal potassium hydroxide within 50 hours or less. The solid urea-base mixtures of this invention preferably contain sufficient strong base to reduce both the biuret content and biuret/urea ratio by at least 50 percent at 60° C. within 100 hours or less.

In most applications base concentration, pH, temperature and reaction time should be correlated to achieve a reduction of initial biuret level of at least about 25 percent, preferably at least about 50 percent. A presently preferred combination of process conditions includes pH levels of at least about 13 and initial base concentration of at least about 0.8 N sufficient to decrease the biuret/urea ratio of a solution initially containing about 0.05 to about 2 weight percent biuret by a factor of at least 2 at a temperature between 20° C. and 65° C. Conditions within these ranges, when correlated with the desired results by the sample test described above, can reduce biuret to less than 75, usually less than 50 and preferably, less than 20 percent of its initial value.

Product biuret levels below about 1 weight percent based on urea can be easily obtained with feeds containing significantly higher biuret levels. However, in most cases, lower levels are desired; e.g., less than 0.5, preferably less than 0.25 (the "low biuret" industry standard), or even below 0.1 weight percent.

The costs of achieving biuret levels below 0.05 weight percent are justifiable in some cases. These levels produce essentially no symptoms of biuret toxicity even in relatively sensitive crops such as lemons and grapefruit. We have demonstrated the ability of this method to reduce biuret to levels even below 0.001 weight percent.

One unique aspect of these methods is their ability to eliminate biuret with little or no urea conversion or loss of nutrient value. Even when some urea is converted, its nitrogen fertilizer value is not lost. The urea decomposition products are usable ammonic nitrogen compounds, and biuret is converted to urea.

We have demonstrated that biuret can be reduced to less than 5 percent of its initial value with nominal, or undetectable urea conversion of less than 5 percent and even less than 1 percent. Even when using high base concentrations and high temperatures; e.g., 80° C., required to obtain rapid biuret reaction rates and short reaction time, greater than 95 percent biuret reduction with urea conversions of less than 10 percent can be achieved.

Urea conversion products, when present, remain in solution, and are "fixed" in solution as usable ammonic nitrogen by neutralization. Thus, the methods of the invention can reduce biuret level by more than 95 percent and yet cause less than 2 percent, and even less than 1 percent loss in initial total nitrogen content (combined urea, ammonic, and biuret nitrogen).

The reaction can be run to completion at a pH above 12.5; e.g., 13.5 to 14, and then neutralized. In the alternative, reaction conditions, e.g., initial base concentration, temperature and target biuret level can be correlated so that the desired biuret level is obtained as the base required to maintain a pH above 12.5 is consumed. Thus, reaction end point will be indicated by a decrease in solution pH to a predetermined level; e.g., 12.5 to 13.

The solution can then be shipped or stored in this condition (after cooling if required). However, we presently prefer to neutralize the solution at this or a later stage of the process. Neutralization converts ammonia produced during the reaction to ammonic salts of the neutralizing acid and converts other bases that may be present; e.g., carbonates, the reactant base (KOH, NaOH, etc.), and others.

Essentially any organic or inorganic acid can be used for neutralization. Mineral acids are preferred due to their nominal cost, availability, and the fact that several mineral acids; e.g., sulfuric and nitric acids, contain anions that also have nutrient value.

The amount of acid required for the desired degree of neutralization can be determined by continuously monitoring solution pH during acid addition. In the alternative, an amount of acid sufficient to neutralize all of the base initially added can be used; this would be approximately equivalent to the amount required to obtain a pH of about 7. Although most of the added base may be consumed during reaction, we have found that it is converted to a weaker base—the corresponding carbonate. The carbonate remains in solution and neutralizes added acid.

The operator should exercise caution during the neutralization step for at least two reasons. Concentrated acid elevates solution temperature and, if added too rapidly, may increase solution temperature beyond tolerable apparatus or process control limits. Secondly, carbonate neutralization causes carbon dioxide evolution which can produce foaming and volume expansion. This effect can be controlled by gradual acid addition and adequate mixing. Antifoaming agents can also be added if desired.

FIG. 1 illustrates suitable vessels 1, 3 and 4 for containing urea, base and acid feeds respectively. Urea and base can be passed via pipes 23 and 5 to batch reactor 7 provided with agitator 8 and thermocouple or other temperature monitoring means 28. Alternatively, the urea feed can be passed to the reaction vessel via pipe 20, ion exchange vessel 19, pipe 21 and valve 22 to remove carbonate as described above. In this alternative valve 2 in pipe 23 would be closed to prevent bypassing.

The mixture in reactor 7 can be recycled during either the biuret reaction or neutralization stages via pipe 9, pump 10 and pipes 17 and 18. Alternatively, it can be recycled through heat exchanger 13 and pipes 16 and 18 by closing valve 25 and opening valve 27. Heating or cooling fluid is added to exchanger 13 via line 14 and removed at 15 to maintain the desired reaction or neutralization temperature in vessel 7.

Following completion of the biuret removal reaction, the desired amount of acid is added to vessel 7 from supply tank 4 via pipe 6. After neutralization is complete, the neutralized mixture can either be cooled further in vessel 7 by recycling through heat exchanger 13 or it can be passed to product accumulator 11 by closing valve 24 and opening 26.

The invention is further described by the following examples which are illustrative of specific modes of practicing the invention and are not intended as limiting the scope of the invention defined by the appended claims.

EXAMPLE I

A reaction mixture is prepared by dissolving 1.6 grams sodium hydroxide (0.04 mole) and 45 grams of urea (0.75 mole) containing 1.76 weight percent of biuret based on urea in sufficient water to obtain a solution volume of 100 ml. The resulting solution is divided into a number of three-ml. aliquots contained in capped vials which were then placed in a constant temperature bath maintained at 45°±0.1° C. As the reaction progressed, representative aliquots were removed and acidified with three ml. of 1 N HCl to terminate the reaction.

Quenched samples are then analyzed simultaneously for urea and biuret by high performance liquid chromatography. After 182 hours the biuret level is reduced to 0.05 weight percent based on urea while the concentration of urea in the reactant solution remains constant. Thus, biuret is selectively removed by our process; biuret concentration being reduced from its initial value of 1.76 weight percent to a final concentration of only 0.05 weight percent based on urea.

EXAMPLE II

A reactant solution is prepared by dissolving 4.8 grams of sodium hydroxide (0.12mole) and 45 grams of urea containing 1.76 weight percent of biuret in sufficient water to obtain a total reactant volume of 100 ml. The solution is divided into three-ml. aliquots which are maintained at a constant temperature of 60° C. in capped vials as described in Example I. Representative aliquots are periodically neutralized and analyzed as described in Example I to establish the progress of the reaction. Biuret concentration is reduced to a level below detection limits within 48 hours. The detection limit is approximately 0.01 weight percent biuret based on urea.

EXAMPLE III

One hundred ninety four pounds of urea (0.96 weight percent biuret based on urea dry weight), 34.8 pounds of 50 percent potassium hydroxide, and 236 pounds of water are added to a 90 gallon reaction vessel provided with a sealable cover, thermostatically controlled heating element and recirculating pump. The temperature of the solution is maintained at 58°±1° C. for 56 hours using continuous recirculation at the rate of approximately 5 gallons per minute. The apparatus is then vented and the reactant solution mixed with 40 pounds of 70 percent nitric acid added through the recirculating line. The reaction product contains 19 weight percent total nitrogen, 2.9 weight percent potassium expressed as $K_2O$, and less than 0.05 weight percent biuret based on urea dry weight.

EXAMPLE IV

One hundred pounds of dry urea particles, e.g., pellets or prills, containing about one weight percent biuret and nine pounds of potassium hydroxide dispersed within the urea particles (1.78 equivalents per kilogram of urea) can be converted to a low biuret urea solution containing less than 0.05 weight percent biuret (based on urea dry weight) by dissolving the particles in 120 pounds of water and maintaining the resulting solution at about 60° C. for 55 hours. If desired, excess unreacted base contained in the reactant solution can be neutralized by adding about 20 pounds of 70 percent nitric acid.

EXAMPLE V

A low biuret urea solution containing less than about 0.2 weight percent biuret (based on urea dry weight) can be obtained by treating the solid mixture of urea and potassium hydroxide described in Example IV under the conditions described in that example within a reaction time of 40 hours.

While particular embodiments of the invention have been described, it will be understood that the invention is not limited thereto since many variations and modifications of the concepts of this invention will be apparent to one skilled in the art in view of the aforegoing disclosure, the drawing, and the appended claims, and it is intended that the invention includes all such modifications and variations that fall within the scope of the claims.

Having now described the invention, we claim:

1. A composition comprising an aqueous urea solution containing at least about 1 weight percent urea, biuret, at least 0.2 N concentration of a strong base capable of producing a pH of at least about 13 in aqueous media sufficient to maintain a pH in said solution of at least about 13, said pH and base concentration being sufficient to reduce both the biuret concentration and the biuret/urea ratio in the said solution at a temperature within the range of about 20° C. to about 65° C.

2. The composition defined in claim 1 wherein said aqueous solution comprises at least about 10 weight percent urea, and at least about a 0.4 N concentration of a base selected from one or more alkali metal hydroxides.

3. The composition defined in claim 2 containing at least about 20 weight percent urea, and said base is selected from the group consisting of sodium hydroxide and potassium hydroxide, and combinations thereof.

4. A composition comprising solid urea, biuret, and at least about 0.2 equivalents per kilogram of urea of a basic component selected from the group consisting of strong bases and strong base precursors that convert to the corresponding strong base when dissolved in water, and combinations thereof, said basic component being capable of producing a pH of at least about 13 in water and being present in said composition at a concentration sufficient to decompose at least a portion of said biuret and produce an aqueous urea solution having a biuret/urea ratio less than the biuret/urea ratio of said composition when said composition is dissolved in water and maintained at a temperature of about 20° C. to about 80° C. for at least about one hour.

5. The composition defined in claim 4 consisting essentially of urea, biuret, and a member selected from the group consisting of mineral and organic bases and combinations thereof, and containing at least about 0.4 equivalents per kilogram of urea of a basic component selected from alkali metal hydroxides and hydroxide precursors, and combinations thereof dispersed in said solid urea.

6. The composition defined in claim 5 wherein said basic component is selected from the group consisting of sodium and potassium hydroxides and hydroxide precursors, and combinations thereof.

7. The composition defined in claim 5 comprising an amount of said basic component sufficient to provide a base concentration of at least about 0.2 N when said composition is dissolved in water in an amount corresponding to a urea concentration of at least about 20 weight percent, and said basic component is selected from the group consisting of potassium oxide and potassium hydroxides, and combinations thereof.

8. A composition comprising solid urea containing biuret and a member selected from the group consisting of mineral and organic bases, and at least about 0.4 equivalents per kilogram of urea of a member selected from the group consisting of sodium and potassium hydroxides, and hydroxide precursors, and combinations thereof.

9. A method for reducing the biuret content of urea containing biuret, which method comprises contacting said urea and biuret in aqueous solution at a temperature between about 0° C. and about 100° C. for a period of at least about four hours with a strong base capable of producing a pH of at least about 12.5, the concentration of said base being sufficient to maintain a pH of at least about 12.5 during said period and to reduce the biuret concentration and decrease and biuret/urea ratio in said solution.

10. The method defined in claim 9 wherein said solution comprises at least about 1 weight percent of said urea, and at least about a 0.1 N concentration of a strong base capable of producing a pH of at least about 13 in said solution, and wherein said base concentration is maintained at a level sufficient to maintain a pH of at least about 13 in said solution for a reaction time sufficient to reduce the biuret content of said solution (a) to less than about 50 percent of its original level and (b) to a level of less than about 0.5 weight percent based on urea.

11. The method defined in claim 9 wherein said solution contains between about 5 to about 85 weight percent urea and at least a 0.2 N concentration of a strong mineral base capable of producing a pH of at least about 13 in said solution, and said solution is maintained at a pH of at least about 13 and a temperature of at least about 20° C. for a period of at least about 10 hours sufficient to produce a treated solution containing less than about 0.5 weight percent biuret based on urea.

12. The method defined in claim 11 wherein said treated solution is neutralized by adding thereto sufficient acid to produce a pH of about 7.5 or less.

13. The method defined in claim 9 wherein said solution comprises at least about 20 weight percent urea, and at least about a 0.2 N alkali metal base concentration, and wherein said solution is maintained at a pH of at least about 13 and a temperature of about 20° C. to about 65° C. for a reaction period of at least about 10 hours sufficient to reduce the biuret concentration of said solution.

14. The method defined in claim 13 further comprising the step of neutralizing the resulting solution of reduced biuret content by adding thereto an amount of a mineral acid sufficient to reduce the pH of said solution to less than about 7.5 and convert at least a portion of the ammonium ion present in said solution to ammonium salts of said acid.

15. The method defined in claim 13 wherein at least about 50 percent of said base is selected from the group consisting of sodium hydroxide and potassium hydroxide and combinations thereof, sufficient base is added to said solution at the beginning of or during said reaction period to maintain the pH of said solution at a level of about 14, and said solution is maintained at said pH and at a temperature of about 40° C. to about 60° C. for said reaction period of at least about 10 hours.

16. A method for reducing the biuret content of urea containing biuret, which method comprises contacting said urea and biuret in an aqueous solution comprising at least about 5 weight percent of said urea and at least about a 0.2 N concentration of base selected from the group consisting of sodium and potassium hydroxides and combinations thereof sufficient to produce a pH of at least about 13, at a temperature of about 20° C. to about 65° C. for at least about 10 hours.

17. A method of reducing the biuret urea ratio of the solid composition defined in claim 4 including the steps of dissolving said composition in water in an amount corresponding to a urea concentration of at least about 2 weight percent, and maintaining the resulting solution at a temperature of about 20° C. to about 80° C. for a period of at least about 1 hour sufficient to reduce said biuret/urea ratio.

18. The method defined in claim 17 wherein said solid composition comprises at least about 0.4 equivalents per kilogram of urea of a member selected from the group consisting of sodium and potassium hydroxides and hydroxide precursors, and combinations thereof, said composition is dissolved in water in an amount corresponding to a urea concentration of at least about 20 weight percent, and said solution is maintained at a temperature of 40° C. to about 60° C. for a period of at least about 4 hours.

* * * * *